US011497661B1

(12) United States Patent
Sullivan

(10) Patent No.: US 11,497,661 B1
(45) Date of Patent: Nov. 15, 2022

(54) DIAPER CHANGING AND DISPOSAL KIT

(71) Applicant: Norena Tina Sullivan, Oak Lawn, IL (US)

(72) Inventor: Norena Tina Sullivan, Oak Lawn, IL (US)

(*) Notice: Subject to any disclaimer, the term of this patent is extended or adjusted under 35 U.S.C. 154(b) by 659 days.

(21) Appl. No.: 16/422,767

(22) Filed: May 24, 2019

Related U.S. Application Data

(60) Provisional application No. 62/762,878, filed on May 25, 2018.

(51) Int. Cl.
A61F 13/42 (2006.01)
A61F 13/551 (2006.01)

(52) U.S. Cl.
CPC .......... *A61F 13/5519* (2013.01); *A61F 13/42* (2013.01); *A61F 13/5512* (2013.01); *A61F 2013/55125* (2013.01)

(58) Field of Classification Search
CPC .. A61F 13/42; A61F 13/5512; A61F 13/5519; A61F 2013/422; A61F 2013/55125
USPC .................................................. 604/385.06
See application file for complete search history.

(56) References Cited

U.S. PATENT DOCUMENTS

| D380,829 S | 7/1997 | Breault | |
| 5,702,379 A * | 12/1997 | Preiss | A61F 13/49017 206/581 |
| D476,741 S | 7/2003 | Childress | |
| 7,569,038 B1 * | 8/2009 | Salem, Jr. | A61F 13/15252 604/385.01 |
| 8,292,863 B2 * | 10/2012 | Donoho | A61F 13/5512 604/385.06 |
| D692,558 S | 10/2013 | Cassano | |
| D733,872 S | 7/2015 | Beck | |
| D762,849 S | 8/2016 | Davenport | |
| 9,532,911 B2 * | 1/2017 | Amiri | A61F 13/5519 |
| D788,294 S | 5/2017 | Cardenas et al. | |
| 9,827,151 B1 * | 11/2017 | Curtis | A61F 13/49017 |
| D813,382 S | 3/2018 | Guadron | |
| D839,420 S | 1/2019 | Williams | |
| D841,800 S | 2/2019 | Saadia | |
| D874,072 S | 1/2020 | Bui | |
| D882,769 S | 4/2020 | Hirsch | |
| D899,732 S | 10/2020 | Foley | |
| D903,237 S | 12/2020 | Speciale et al. | |
| D906,627 S | 1/2021 | Cammarota et al. | |

(Continued)

OTHER PUBLICATIONS

Storks & Berries retail website; "Baby Kangas One-Size Pouch Diaper" product listing; https://storksandberries.ca/Baby-Kangas-One-Size-Pouch-Diaper-with-Insert-Cotton-Candy-Pink (last accessed Oct. 15, 2019).

(Continued)

*Primary Examiner* — Catharine L Anderson
(74) *Attorney, Agent, or Firm* — Brie A. Crawford; Crawford Intellectual Property Law LLC

(57) ABSTRACT

A diaper changing and disposal kit is disclosed. The diaper changing and disposal kit has a diaper with a pocket. The pocket stores a variety of diaper changing supplies such as baby wipes, disposable gloves, and an airtight disposal bag. The diaper also has a wetness indicator strip to aid a user in determining when the diaper needs to be changed. Preferably, the diaper changing and disposal kit is stored in a package until it is ready to be used.

2 Claims, 5 Drawing Sheets

(56) References Cited

U.S. PATENT DOCUMENTS

| | | | |
|---|---|---|---|
| D908,314 S | 1/2021 | Charlot | |
| D919,233 S | 5/2021 | Johnson | |
| D924,542 S | 7/2021 | Clear | |
| 2002/0004656 A1* | 1/2002 | Khan | A61F 13/84 604/385.06 |
| 2004/0092901 A1* | 5/2004 | Reece | A61F 13/84 604/385.06 |
| 2006/0264858 A1* | 11/2006 | Roe | A61F 13/42 604/361 |
| 2006/0282056 A1* | 12/2006 | McDonald | A61F 13/505 604/385.13 |
| 2008/0086103 A1* | 4/2008 | McKiernan | G01K 11/165 604/385.02 |

OTHER PUBLICATIONS

Nicki's Diapers retail website; "BabyKicks Organic One Size Fitted Diaper" product listing; https://www.nickisdiapers.com/babykicks-organic-diapers-one-size.html (last accessed Oct. 15, 2019).

Dirty Diaper Laundry website; "BumGenius 3.0 Review"; https://dirtydiaperlaundry.com/bum-genius-3-0-review (last accessed Oct. 15, 2019).

Green Diaper Store retail website; "Happy Heinys One Size Pocket Diaper" product listing; https://www.greendiaperstore.com/happy-heinys-one-size-pocket-diaper.html (last accessed Oct. 15, 2019).

* cited by examiner

DIAPER CHANGING AND DISPOSAL KIT

CROSS REFERENCE TO RELATED APPLICATION AND INCORPORATION BY REFERENCE

This application claims priority to and is a continuation-in-part of the previously filed United States of America Provisional Patent Application titled "POO PACK AUNTIE BABIES" with an application filing date of May 25, 2018 in the United States Patent and Trademark Office, with Application No. 62/762,878 by the same inventive entity. The entirety of Application No. 62/762,878 being incorporated herein by reference to provide continuity of disclosure.

This invention relates to a diaper changing and disposal kit and more particularly to a diaper changing and disposal kit that has a diaper with a pocket, baby wipes, gloves, an airtight disposal bag, and a wetness indicator strip. A method for using the diaper changing and disposal kit is also disclosed.

BACKGROUND OF THE INVENTION

In today's world, many parents and families are on the go. When a parent is leaving the house, baby supplies are needed and babies require numerous supplies. This can be a cumbersome process as the parents or other caretakers have to gather the supplies and place the supplies in a diaper bag or other carrying receptacle. Once the parents or other caretakers get to the desired location, the bag or receptacle with the supplies has to be carried in transport or to the destination. If the parents or other caretakers are going to a park, museum, shopping establishment, or other establishment or event, they may have to carry the bag or receptacle around the entire day. The bag or receptacle can be cumbersome, heavy, or burdensome. A diaper changing kit that is portable and easy to pack and carry will be a useful invention.

Family members and other caretakers may also have the baby with them while in transit. While a parent may have a pre-packed diaper bag or other receptacle and the supplies readily available, a caretaker such as an aunt or uncle may not. It can be inconvenient for a non-parent caretaker to purchase these supplies, and then transport them. Also, it can be expensive for a non-parent caretaker to purchase the supplies as they are normally sold separately and are sold in larger quantities or volumes. The non-parent caretaker may only use a small portion of the purchased supplies. A diaper changing kit that provides the essentials for changing a diaper that is portable and easy to transport will be a useful invention.

Moreover, it can be difficult to determine if a diaper needs changed without taking off the diaper. This is inconvenient at home and especially inconvenient in public places. A diaper that has a wetness indicator to determine if a diaper needs to be changed will be a useful invention.

Also, changing a diaper in a public place, such as a public restroom, can have sanitary issues. Once a soiled diaper is changed, it has to be disposed of. Also, changing a diaper in general can raise sanitary concerns for the baby as well as the caretaker. The baby and caretaker can transfer microorganisms or diseases between each other. A diaper changing kit that provides the essentials for changing a diaper in a sanitary manner will be a useful invention.

SUMMARY OF THE INVENTION

An objective of the present invention is the provision of a diaper changing and disposal kit that has a diaper, baby wipes, disposable sanitary gloves, an airtight disposal bag, and a wetness indicator strip.

Another objective of the present invention is the provision of a diaper changing and disposal kit that has a diaper with a pocket to store the wipes, disposable sanitary gloves, airtight disposal bag, and other diaper changing supplies in a portable manner.

A still further objective of the present invention is the provision of a diaper changing and disposal kit that has a wetness indicator strip to determine if the diaper needs to be changed.

Moreover, an objective of the present invention is the provision of a method of using a diaper changing and disposal kit.

These and other objectives of the invention (which other objectives become clear by consideration of the specification, drawings, and claims as a whole) are met by the present invention.

BRIEF DESCRIPTION OF THE DRAWINGS

Throughout the figures of the drawings, where the same part appears in more than one figure of the drawings, the same number is applied thereto.

DETAILED DESCRIPTION OF THE PREFERRED EMBODIMENTS

Figure 1:
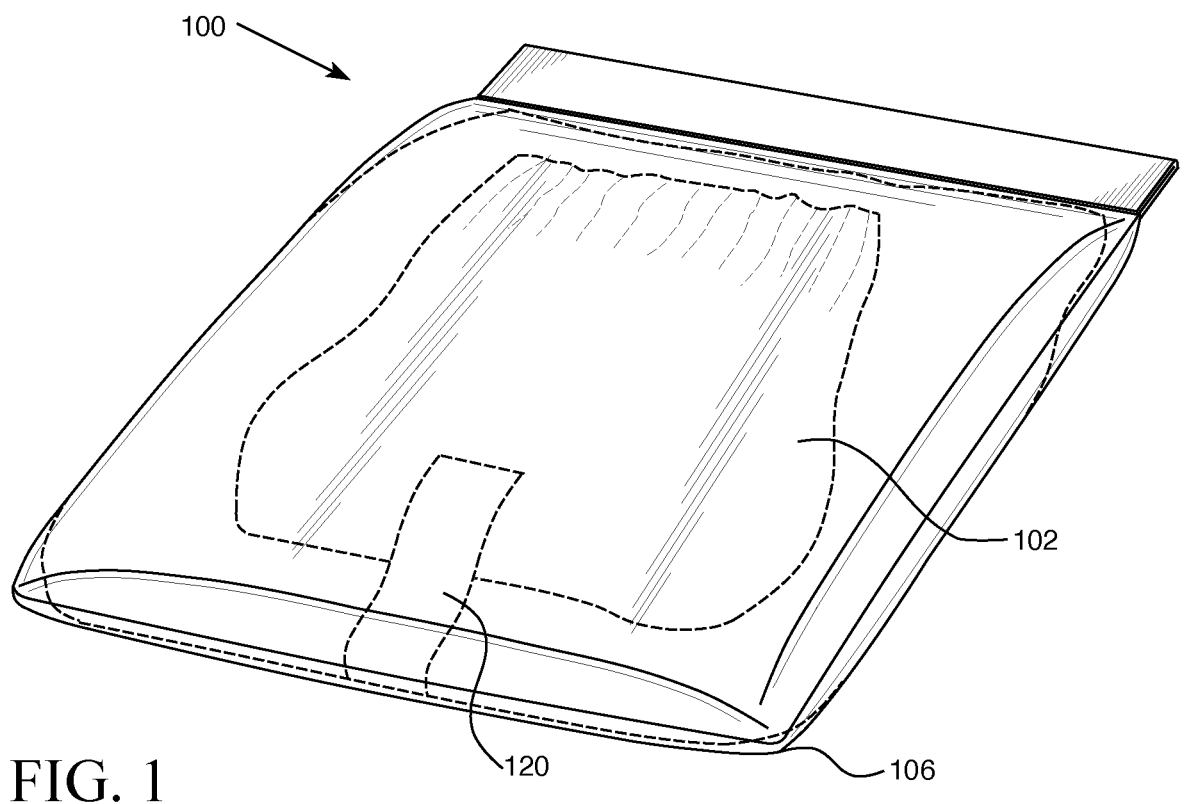
FIG. 1 depicts a rear perspective view of the diaper changing and disposal kit 100 of this invention.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, over, above, below, beneath, rear, and front, may be used with respect to the drawings. These and similar directional terms are not to be construed to limit the scope of the invention in any manner. The words attach, connect, couple, and similar terms with their inflectional morphemes do not necessarily denote direct or intermediate connections, but may also include connections through mediate elements or devices.

Throughout the description the term baby is used as the person wearing the diaper to be changed. However, the person wearing the diaper does not necessarily have to be a baby, but can include older children who wear diapers. Also, the person wearing the diaper may be an adult. The term baby is meant to encompass any person, of any age, that is wearing diapers and all such persons are encompassed by this disclosure.

Diaper 102 can be of any suitable structure. It is preferred that diaper 102 have a front section connected to a rear section through a center crotch section. Diaper 102 also has two leg apertures. There is an absorbent layer between the interior layer of the diaper 102 which contacts the baby's skin and the exterior layer of the diaper 102.

Figure 2:
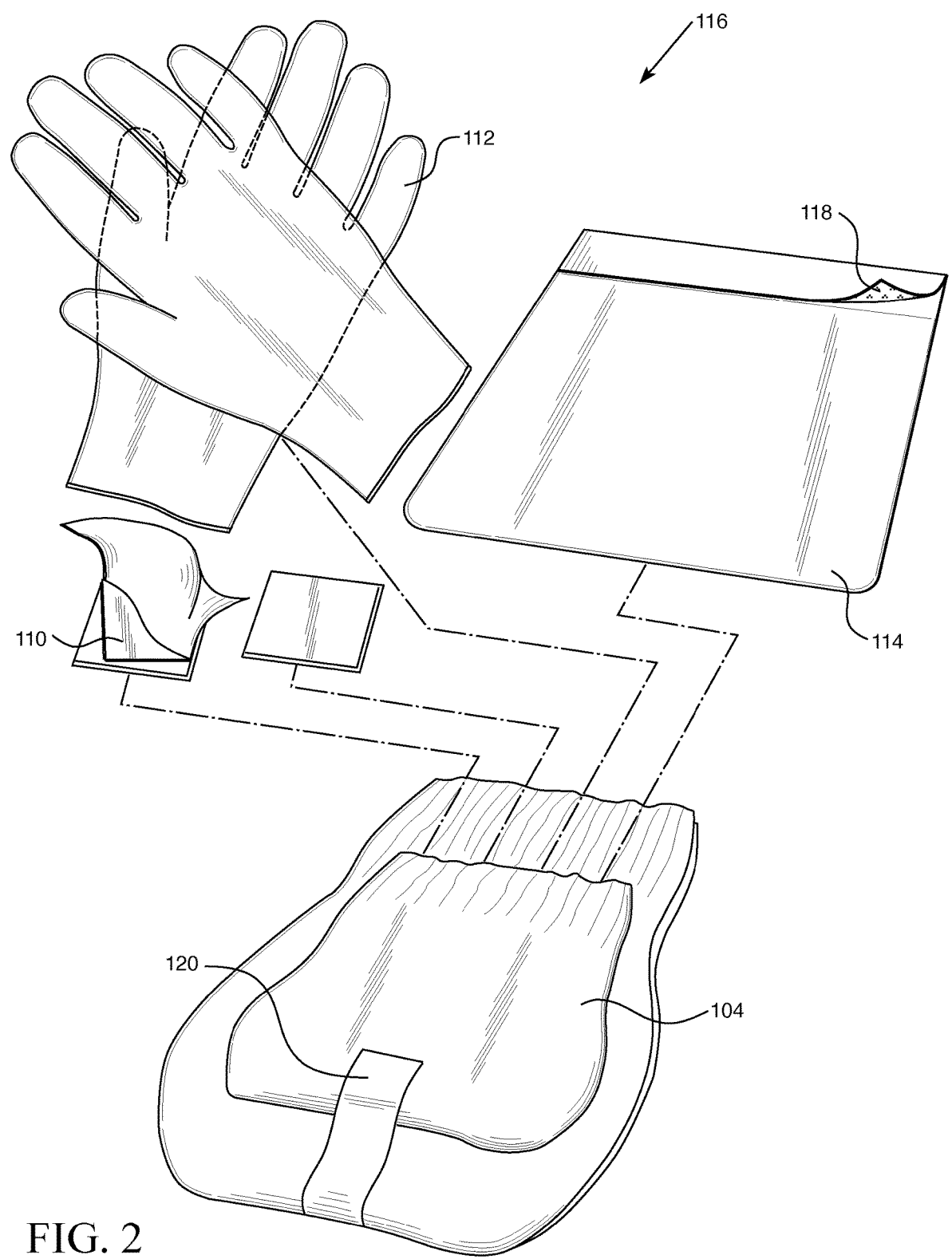
FIG. 2 depicts an exploded perspective view of the contents of the diaper changing and disposal kit 100 with folded diaper 102, wipes 110, disposable gloves 112, and airtight disposal bag 114.
Figure 3:
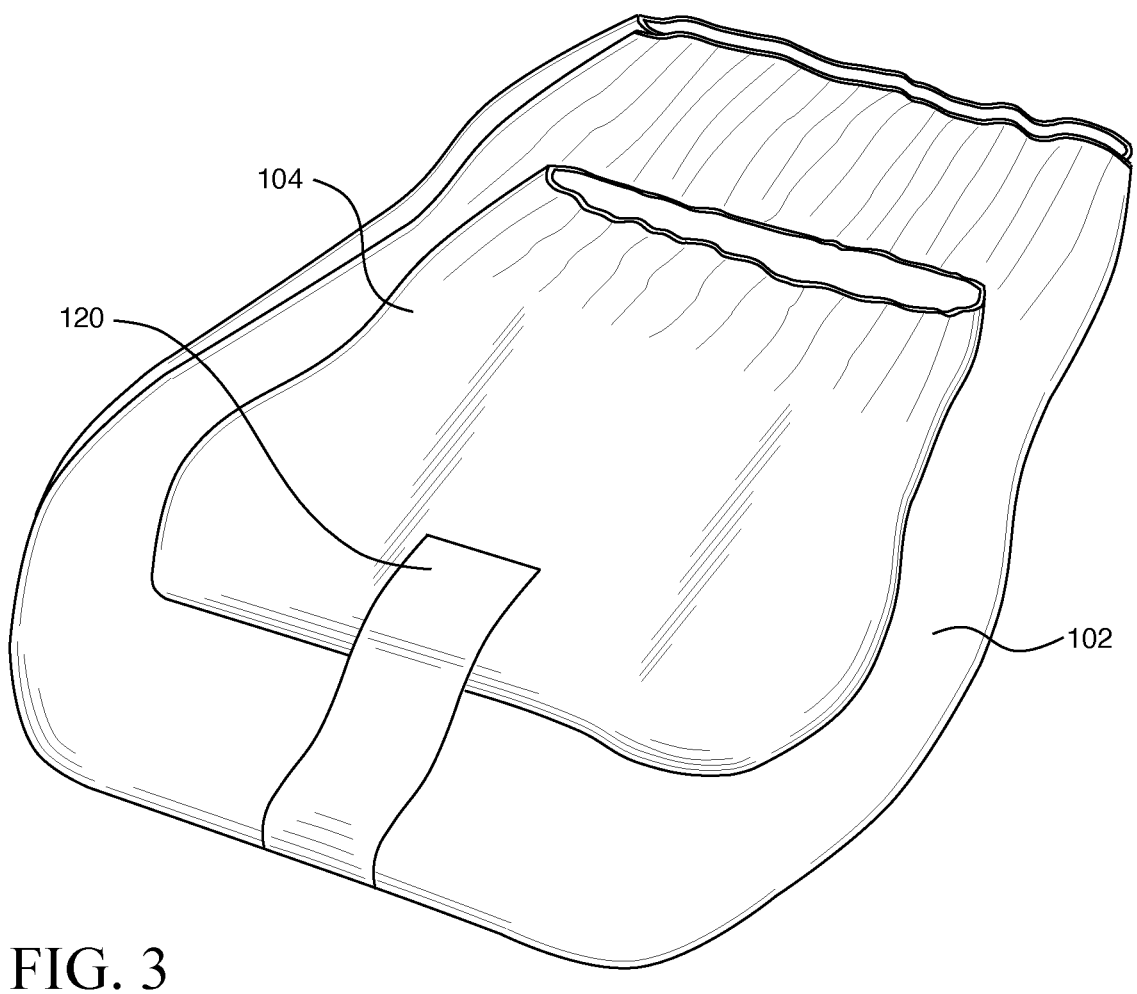
FIG. 3 depicts a rear perspective view of folded diaper 102 with pocket 104 and wetness indicator strip 120.
Figure 4:
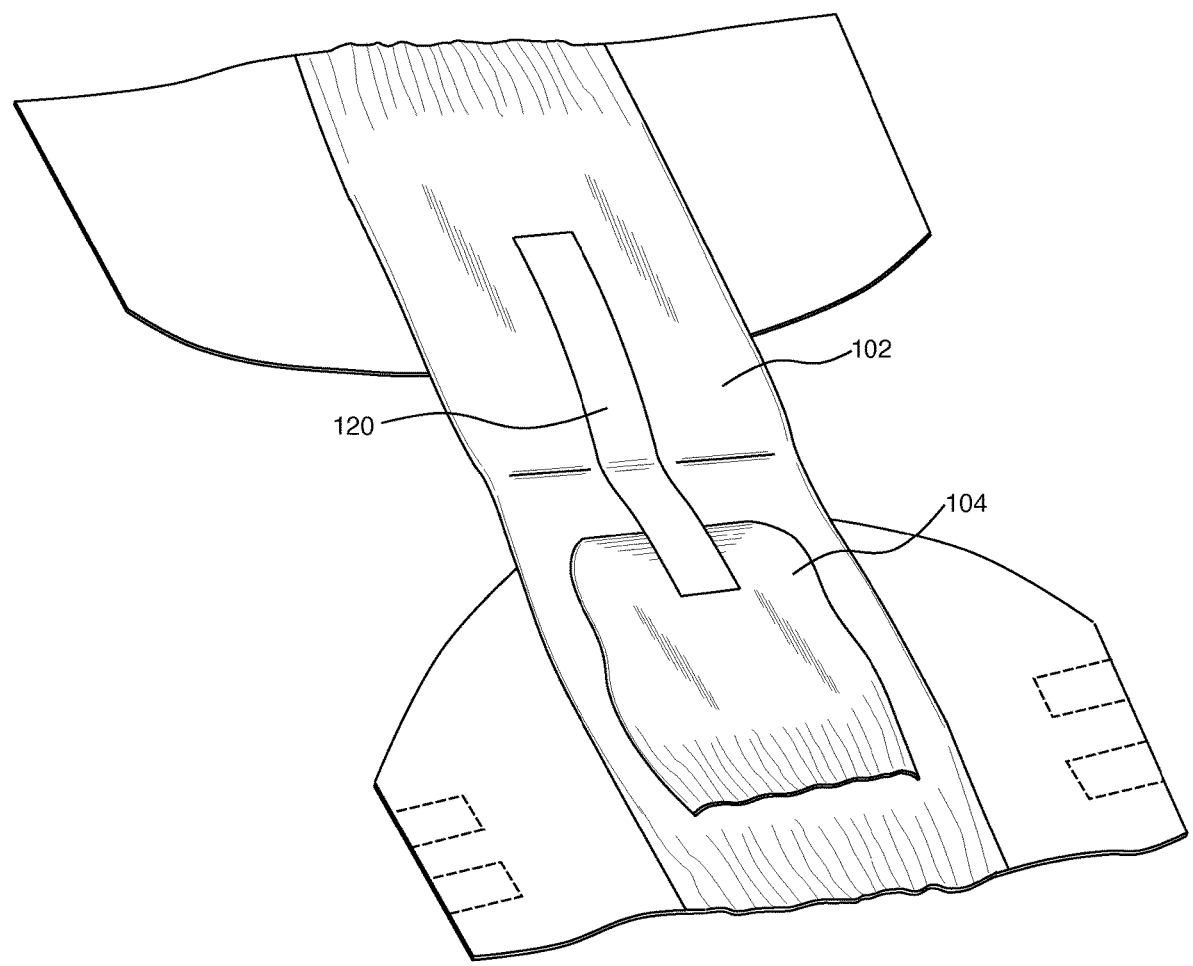
FIG. 4 depicts a top perspective view of unfolded diaper 102 with pocket 104 and wetness indicator strip 120.
Figure 5:
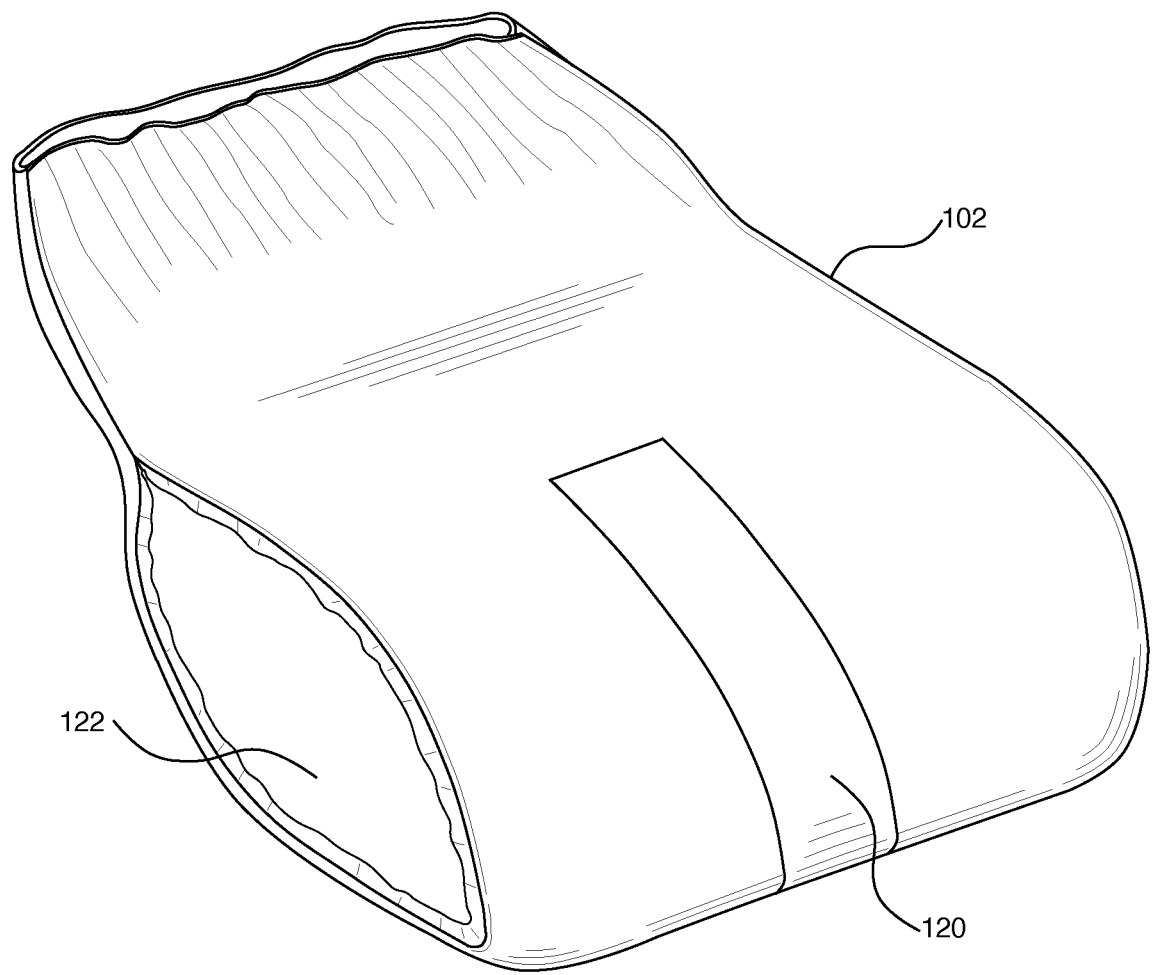
FIG. 5 depicts a front perspective view of folded diaper 102 with wetness indicator strip 120.

Now adding FIG. 1, FIG. 2, and FIG. 3 to the consideration, the structure and function of diaper changing and disposal kit 100 can be clearly seen. Diaper changing and disposal kit 100 has diaper 102, baby wipes 110, disposable gloves 112, and airtight disposal bag 114. Diaper changing and disposal kit 100 is preferably contained in package 106 until diaper changing and disposal kit 100 is desired to be used. Package 106 helps to keep diaper changing and disposal kit 100 with diaper 102, baby wipes 110, disposable gloves 112, and airtight disposal bag 114 contained and makes the diaper changing and disposal kit 100 easy to transport.

Baby wipes 110, disposable gloves 112, and airtight disposal bag 114 are collectively referred to as diaper changing supplies 116. While baby wipes 110, disposable gloves 112, and airtight disposal bag 114 are the preferred diaper changing supplies 116, other supplies can be included such as baby lotion, baby powder, diaper rash cream and all appropriate supplies necessary for changing a diaper 102 are encompassed by this disclosure. It is preferred, but not required, that baby wipes 110 are contained in individual sealed packages.

Diaper changing and disposal kit 100 has diaper 102. Diaper 102 has pocket 104. Pocket 104 is able to hold baby wipes 110, disposable gloves 112, and airtight disposal bag 114. Other baby changing supplies 116 may also be contained in pocket 104.

It is preferred, but not required, that pocket 104 is on the exterior of the rear side of diaper 102. But, the pocket 104 can be placed on any portion of diaper 102 as long as it does not interfere with the use or function of diaper 102.

Diaper 102 also has wetness indicator strip 120. Wetness indicator strip 120 helps indicate when the diaper 102 has been soiled by wetness and needs to be changed. It is preferred, but not required, that wetness indicator strip 120 have a first or original color which indicates that diaper 102 does not need to be changed and then, wetness indicator strip 120 changes to a second color indicating that diaper 102 now needs to be changed. For example, wetness indicator strip 120 can start off yellow to indicate that the diaper 102 does not need to be changed. Then, the wetness indicator strip 120 can turn green once the baby soils the diaper 102 to indicate that the diaper 102 now needs to be changed.

It is preferred, but not required, that the wetness indicator strip 120 extend from the lower one fourth of the pocket 104 and extend through the center crotch section of the diaper 102 to the front lower one half of the diaper 102. But, any placement of wetness indicator strip 120 that allows the strip 120 to function, but does not interfere with the function of diaper 102 can be utilized and is encompassed by this disclosure.

Wetness indicator strip 120 can be embedded on diaper 102, a chemical embedded on diaper 102, a tape or strip that is attached to the surface of diaper 102, a tape or strip that is embedded with chemicals and attached to the surface of diaper 102, or any other suitable means for creating the wetness indicator strip 120 and all such suitable means are encompassed by this disclosure.

It is preferred, but not required, that the wetness indicator strip 120 be positioned on the exterior of the diaper 102. Once diaper 102 is soiled beyond what it can absorb, the urine soaks through the interior layers 122 of diaper 102 and reaches the wetness indicator strip 120. Interior layers 122 are made of an absorbent material to absorb human waste. For example, the baby can soil the diaper 102 and the interior layers 122 of diaper 102 will absorb the urine and not affect the baby's skin or activate the wetness indicator strip 120. But, once the interior layers 122 can no longer absorb more urine, the urine reaches the wetness indicator strip 120. Once the urine reaches wetness indicator strip 120, diaper 102 can no longer absorb the urine and the urine activates the wetness indicator strip 120 and alerts the caretaker to change diaper 102.

It is preferred, but not required, that airtight disposal bag 114 have an adhesive seal 118. Then, soiled diaper 102, soiled baby wipes 110, and soiled disposable gloves 112 can be placed in airtight disposal bag 114 and the bag 114 can be sealed through adhesive seal 118. In another embodiment, the airtight disposal bag 114 can be a bag with an interlocking strip closure. An example of a bag with an interlocking strip closure is sold under the trade name Ziploc®. Ziploc® is a registered trademark of S.C. Johnson & Son, Inc. with registration number (among others) 0886112.

Diaper changing and disposal kit 100 provides safety and sanitary functions as well. The gloves 112 can reduce the risk of the baby and caretaker transferring microorganisms, viruses, and other diseases to each other. The wetness indicator strip 120 can help reduce the risk of skin irritation and diaper rash because the parent or caretaker can more readily identify when the diaper 102 is soiled and needs to be changed. The airtight disposal bag 114 can reduce costs on other items currently on the market to dispose of soiled diapers 102 because it reduces the odor of the soiled diaper 102 and an example of such item is sold under the trade name Diaper Genie®. Diaper Genie® is a registered trademark of Mondial Industries, Ltd. composed of Hazelbank, Inc with a registration number (among others) of 1827510.

A exemplary method for using the diaper changing and disposal kit 100 is also disclosed. This method is meant to illustrate, but not limit, the user of diaper changing and disposal kit 100 and any suitable method of use is encompassed by this disclosure.

1) A user (the user being a parent, guardian, or other caretaker of a baby and not the person who actually wears the diaper 102) obtains a diaper changing and disposal kit 100;

2) The user stores or transports the diaper changing and disposal kit 100 until the user is ready to use diaper changing and disposal kit 100;

3) When the user wants to use the diaper changing and disposal kit 100, the user opens package 106 (if the kit 100 is in the package 106) and removes the diaper 102 from the package 106;

4) The user removes diaper changing supplies 116 from the pocket 104 of diaper 102;

5) The user places disposable gloves 112 on his or her hands;

6) The user removes the soiled diaper 102 the baby is currently wearing (if any) and places soiled diaper 102 in the airtight disposal bag 114;

7) The user places diaper 102 underneath the baby;

8) The user uses baby wipes 110 to clean the baby and once finished, places the soiled baby wipes 110 in the airtight disposal bag 114; and 9) The user secures diaper 102 to the baby.

10) The user removes disposable gloves 112 from his or her hands and places them in airtight disposal bag 114 and securely closes the airtight disposal bag 114. Airtight disposal bag 114 is preferably sealed with adhesive seal 118 or an interlocking strip closure.

Steps 7 and 8 can be performed in any interchangeable order. Also, if other diaper changing supplies 116 are present, they can be utilized in Step 8 as well.

While various embodiments and aspects of the present invention have been described above, it should be understood that they have been presented by way of example only, and not limitation. Thus, the breadth and scope of the present invention should not be limited by any of the above exemplary embodiments.

This application—taken as a whole with the abstract, specification, claims, and drawings being combined—provides sufficient information for a person having ordinary skill in the art to practice the invention as disclosed herein. Any measures necessary to practice this invention are well within the skill of a person having ordinary skill in this art after that person has made a careful study of this disclosure.

Because of this disclosure and solely because of this disclosure, modification of this method can become clear to a person having ordinary skill in this particular art. Such modifications are clearly covered by this disclosure.

The invention claimed is:

1. A diaper comprising:
a) the diaper having a front side connected to a back side through a center crotch section;
b) the diaper having two leg apertures;
c) the diaper having a pocket, wherein the pocket is able to hold at least one diaper changing supply;
d) the diaper having a wetness indicator strip;
e) the pocket being located on an exterior of the back side of the diaper; and
f) the wetness indicator strip extending from a lower one fourth of the pocket and extending through the center crotch section of the diaper to a front lower one half of the diaper.

2. The diaper of claim 1 further comprising:
a) the wetness indicator strip having a first and a second color, wherein the first color is an original color that indicates that the diaper does not need to be changed and the original color changes to the second color to indicate that the diaper needs to be changed.

\* \* \* \* \*